United States Patent [19]
Tatsumi et al.

[11] Patent Number: 5,814,465
[45] Date of Patent: Sep. 29, 1998

[54] BIOTINATED FIREFLY LUCIFERASE, A GENE FOR BIOTINATED FIREFLY LUCIFERASE, A RECOMBINANT DNA, A PROCESS FOR PRODUCING BIOTINATED LUCIFERASE AND A BIOLUMINESCENT ANALYSIS METHOD

[75] Inventors: Hiroki Tatsumi; Satoshi Fukuda; Mamoru Kikuchi; Yasuji Koyama, all of Noda, Japan

[73] Assignee: Kikkoman Corporation, Noda, Japan

[21] Appl. No.: 460,934

[22] Filed: Jun. 5, 1995

[30] Foreign Application Priority Data

Jul. 27, 1994 [JP] Japan .................................. 6-193798
Mar. 14, 1995 [JP] Japan .................................. 7-054625
Apr. 24, 1995 [JP] Japan .................................. 7-098857

[51] Int. Cl.$^6$ .............................. C12Q 1/66; C12N 9/96; C12N 9/02; G01N 33/566
[52] U.S. Cl. ................................ 435/7.5; 435/7.6; 435/8; 435/188; 435/189
[58] Field of Search ..................................... 435/189, 188, 435/7.5, 8, 7.6

[56] References Cited

U.S. PATENT DOCUMENTS 5,229,285 7/1993 Kajiyama et al. ....................... 435/189
5,252,466 10/1993 Cronan, Jr. ............................. 435/719

FOREIGN PATENT DOCUMENTS 141 581 5/1985 European Pat. Off. .

OTHER PUBLICATIONS

C.S. Thompson et al., "Chimeric Proteins Incorporating an In Vivo Biotinylation Domain", Protein Engineering 6 Suppl.: 70, 1993.
P.J. Schatz, "Use of Peptide Libraries to Map the Substrate Specificity of a Peptide Modifying Enzyme: A 13 Residue Consensus Peptide Specifies Biotinylation in *Escherichia coli*" Biotecnology 1(10): 1138–1143, Oct. 1993.

*Primary Examiner*—Rebecca E. Prouty
*Attorney, Agent, or Firm*—Oblon, Spivak, McClelland, Maier & Neustadt, P.C.

[57] ABSTRACT

The present invention relates to biotinated firefly luciferase comprising a biotinated peptide and firefly luciferase linked therein, biotinated firefly luciferase having a specific amino acid sequence, a biotinated firefly luciferase gene comprising a gene coding for a biotinated peptide and a firefly luciferase gene linked therein, a biotinated firefly luciferase gene comprising a biotinated peptide gene coding for a specific amino acid sequence and a firefly luciferase gene linked therein, a recombinant DNA comprising said biotinated firefly luciferase gene inserted into a vector DNA, a process for producing biotinated firefly luciferase comprising culturing a microorganism belonging to the genus Escherichia carrying said recombinant DNA and then recovering the resulting biotinated firefly luciferase from the culture, a bioluminescent analysis method comprising using said biotinated firefly luciferase, and a bioluminescent analysis method comprising quantifying a ligand by measuring a biotinated receptor by the use of said biotinated firefly luciferase.

According to the present invention, there are provided biotinated firefly luciferase, a biotinated firefly luciferase gene, a recombinant DNA, a process for producing biotinated firefly luciferase and a bioluminescent analysis method. The present invention enables the efficient production of biotinated firefly luciferase of uniform properties with the uniform structure of firefly luciferase in which one biotin molecule has been bound to a specific residue and whose activity is hardly lost by biotination and not lost even binding to streptoavidin or avidin, and the biotinated firefly luciferase of constant properties obtained in the present invention permits highly sensitive measurements in bioluminescent analysis as compared with the conventional chemically modified biotinated firefly luciferase so that the present invention is industrially extremely useful.

10 Claims, 2 Drawing Sheets

LIL : Luciola lateralis luciferase cDNA
84 : biotinated peptide #84
Ap : β-lactamase gene
lacP: β-galactosidase promoter
E : EcoRI    M : MunI
H : HindIII   X : XhoI
Hp : HpaI LIL : Luciola lateralis luciferase cDNA
Ap : β-lactamase gene
lacP: β-galactosidase promoter
E : EcoRI        B : BamHI

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 13
        ( D ) OTHER INFORMATION: /product="Lys-13"
            / note= "Biotinylated by biotin holoenzyme synthetase"

( x i ) SEQUENCE DESCRIPTION: SEQ ID NO:1:

```
Met  Ala  Phe  Ser  Leu  Arg  Ser  Ile  Leu  Glu  Ala  Gln  Lys  Met  Glu  Leu
1                 5                        10                       15

Arg  Asn  Thr  Pro  Gly  Gly  Ser
```

-continued

20

(2) INFORMATION FOR SEQ ID NO:2:

(i) SEQUENCE CHARACTERISTICS:
        (A) LENGTH: 548 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: Luciola lateralis (xi) SEQUENCE DESCRIPTION: SEQ ID NO:2:

```
Met Glu Asn Met Glu Asn Asp Glu Asn Ile Val Tyr Gly Pro Glu Pro
  1               5                  10                  15
Phe Tyr Pro Ile Glu Glu Gly Ser Ala Gly Ala Gln Leu Arg Lys Tyr
                 20                  25                  30
Met Asp Arg Tyr Ala Lys Leu Gly Ala Ile Ala Phe Thr Asn Ala Leu
             35                  40                  45
Thr Gly Val Asp Tyr Thr Tyr Ala Glu Tyr Leu Glu Lys Ser Cys Cys
         50                  55                  60
Leu Gly Glu Ala Leu Lys Asn Tyr Gly Leu Val Val Asp Gly Arg Ile
 65                  70                  75                  80
Ala Leu Cys Ser Glu Asn Cys Glu Glu Phe Phe Ile Pro Val Leu Ala
                 85                  90                  95
Gly Leu Phe Ile Gly Val Gly Val Ala Pro Thr Asn Glu Ile Tyr Thr
            100                 105                 110
Leu Arg Glu Leu Val His Ser Leu Gly Ile Ser Lys Pro Thr Ile Val
            115                 120                 125
Phe Ser Ser Lys Lys Gly Leu Asp Lys Val Ile Thr Val Gln Lys Thr
        130                 135                 140
Val Thr Ala Ile Lys Thr Ile Val Ile Leu Asp Ser Lys Val Asp Tyr
145                 150                 155                 160
Arg Gly Tyr Gln Ser Met Asp Asn Phe Ile Lys Lys Asn Thr Pro Gln
                165                 170                 175
Gly Phe Lys Gly Ser Ser Phe Lys Thr Val Glu Val Asn Arg Lys Glu
            180                 185                 190
Gln Val Ala Leu Ile Met Asn Ser Ser Gly Ser Thr Gly Leu Pro Lys
        195                 200                 205
Gly Val Gln Leu Thr His Glu Asn Leu Val Thr Arg Phe Ser His Ala
    210                 215                 220
Arg Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Leu Thr Cys Gly Phe Arg Ile Val Met Leu Thr Lys Phe Asp Glu
            260                 265                 270
Glu Thr Phe Leu Lys Thr Leu Gln Asp Tyr Lys Cys Ser Ser Val Ile
        275                 280                 285
Leu Val Pro Thr Leu Phe Ala Ile Leu Asn Arg Ser Glu Leu Leu Asp
    290                 295                 300
Lys Tyr Asp Leu Ser Asn Leu Val Glu Ile Ala Ser Gly Gly Ala Pro
305                 310                 315                 320
Leu Ser Lys Glu Ile Gly Glu Ala Val Ala Arg Arg Phe Asn Leu Pro
                325                 330                 335
```

```
            Gly   Val   Arg   Gln   Gly   Tyr   Gly   Leu   Thr   Glu   Thr   Thr   Ser   Ala   Ile   Ile
                              340                     345                           350

Ile   Thr   Pro   Glu   Gly   Asp   Asp   Lys   Pro   Gly   Ala   Ser   Gly   Lys   Val   Val
                        355                           360                           365

Pro   Leu   Phe   Lys   Ala   Lys   Val   Ile   Asp   Leu   Asp   Thr   Lys   Lys   Thr   Leu
                        370                     375                     380

Gly   Pro   Asn   Arg   Arg   Gly   Glu   Val   Cys   Val   Lys   Gly   Pro   Met   Leu   Met
            385                           390                     395                                 400

Lys   Gly   Tyr   Val   Asp   Asn   Pro   Glu   Ala   Thr   Arg   Glu   Ile   Ile   Asp   Glu
                                    405                           410                           415

Glu   Gly   Trp   Leu   His   Thr   Gly   Asp   Ile   Gly   Tyr   Tyr   Asp   Glu   Glu   Lys
                                    420                     425                           430

His   Phe   Phe   Ile   Val   Asp   Arg   Leu   Lys   Ser   Leu   Ile   Lys   Tyr   Lys   Gly
                              435                           440                     445

Tyr   Gln   Val   Pro   Pro   Ala   Glu   Leu   Glu   Ser   Val   Leu   Leu   Gln   His   Pro
                        450                           455                     460

Asn   Ile   Phe   Asp   Ala   Gly   Val   Ala   Gly   Val   Pro   Asp   Pro   Ile   Ala   Gly
            465                           470                           475                           480

Glu   Leu   Pro   Gly   Ala   Val   Val   Val   Leu   Glu   Lys   Gly   Lys   Ser   Met   Thr
                                    485                           490                           495

Glu   Lys   Glu   Val   Met   Asp   Tyr   Val   Ala   Ser   Gln   Val   Ser   Asn   Ala   Lys
                              500                           505                           510

Arg   Leu   Arg   Gly   Gly   Val   Arg   Phe   Val   Asp   Glu   Val   Pro   Lys   Gly   Leu
                        515                           520                           525

Thr   Gly   Lys   Ile   Asp   Gly   Lys   Ala   Ile   Arg   Glu   Ile   Leu   Lys   Lys   Pro
                        530                           535                           540

Val   Ala   Lys   Met
            545
```

( 2 ) INFORMATION FOR SEQ ID NO:3:

( i ) SEQUENCE CHARACTERISTICS:
      ( A ) LENGTH: 85 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "Synthetic DNA
          oligonucleotide SLF69"

( x i ) SEQUENCE DESCRIPTION: SEQ ID NO:3:

```
ATGGCATTTT   CATTACGTTC   TATTCTTGAA   GCTCAAAAAA   TGGAATTACG   TAACACTCCA        60

GGAGGTAGTC   TCGAGGCTAC   AATTG                                                    85
```

( 2 ) INFORMATION FOR SEQ ID NO:4:

( i ) SEQUENCE CHARACTERISTICS:
      ( A ) LENGTH: 85 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "Synthetic DNA
          oligonucleotide SLF70"

( x i ) SEQUENCE DESCRIPTION: SEQ ID NO:4:

```
CAATTGTAGC   CTCGAGACTA   CCTCCTGGAG   TGTTACGTAA   TTCCATTTTT   TGAGCTTCAA        60

GAATAGAACG   TAATGAAAAT   GCCAT                                                    85
```

( 2 ) INFORMATION FOR SEQ ID NO:5:

( i ) SEQUENCE CHARACTERISTICS:
    ( A ) LENGTH: 1704 base pairs
    ( B ) TYPE: nucleic acid
    ( C ) STRANDEDNESS: double
    ( D ) TOPOLOGY: unknown ( i i ) MOLECULE TYPE: DNA (genomic)

( i x ) FEATURE:
    ( A ) NAME/KEY: CDS
    ( B ) LOCATION: 1..1704

( i x ) FEATURE:
    ( A ) NAME/KEY: misc_feature
    ( B ) LOCATION: 1..1704
    ( D ) OTHER INFORMATION: /note= "Nucleotide sequence of the
      biotinylated firefly luciferase gene contained in
      recombinant plasmid pHLf203 DNA"

( x i ) SEQUENCE DESCRIPTION: SEQ ID NO:5:

```
ATG GCA TTT TCA TTA CGT TCT ATT CTT GAA GCT CAA AAA ATG GAA TTA       48
Met Ala Phe Ser Leu Arg Ser Ile Leu Glu Ala Gln Lys Met Glu Leu
 1               5                  10                  15

CGT AAC ACT CCA GGA GGT AGT CTC GAG AAC GAT GAA AAT ATT GTG TAT       96
Arg Asn Thr Pro Gly Gly Ser Leu Glu Asn Asp Glu Asn Ile Val Tyr
             20                  25                  30

GGT CCT GAA CCA TTT TAC CCT ATT GAA GAG GGA TCT GCT GGA GCA CAA      144
Gly Pro Glu Pro Phe Tyr Pro Ile Glu Glu Gly Ser Ala Gly Ala Gln
         35                  40                  45

TTG CGC AAG TAT ATG GAT CGA TAT GCA AAA CTT GGA GCA ATT GCT TTT      192
Leu Arg Lys Tyr Met Asp Arg Tyr Ala Lys Leu Gly Ala Ile Ala Phe
     50                  55                  60

ACT AAC GCA CTT ACC GGT GTC GAT TAT ACG TAC GCC GAA TAC TTA GAA      240
Thr Asn Ala Leu Thr Gly Val Asp Tyr Thr Tyr Ala Glu Tyr Leu Glu
 65                  70                  75                  80

AAA TCA TGC TGT CTA GGA GAG GCT TTA AAG AAT TAT GGT TTG GTT GTT      288
Lys Ser Cys Cys Leu Gly Glu Ala Leu Lys Asn Tyr Gly Leu Val Val
                 85                  90                  95

GAT GGA AGA ATT GCG TTA TGC AGT GAA AAC TGT GAA GAG TTC TTT ATT      336
Asp Gly Arg Ile Ala Leu Cys Ser Glu Asn Cys Glu Glu Phe Phe Ile
             100                 105                 110

CCT GTA TTA GCC GGT TTA TTT ATA GGT GTC GGT GTG GCT CCA ACT AAT      384
Pro Val Leu Ala Gly Leu Phe Ile Gly Val Gly Val Ala Pro Thr Asn
         115                 120                 125

GAG ATT TAC ACT CTA CGT GAA TTG GTT CAC AGT TTA GGC ATC TCT AAG      432
Glu Ile Tyr Thr Leu Arg Glu Leu Val His Ser Leu Gly Ile Ser Lys
     130                 135                 140

CCA ACA ATT GTA TTT AGT TCT AAA AAA GGA TTA GAT AAA GTT ATA ACT      480
Pro Thr Ile Val Phe Ser Ser Lys Lys Gly Leu Asp Lys Val Ile Thr
145                 150                 155                 160

GTA CAA AAA ACG GTA ACT GCT ATT AAA ACC ATT GTT ATA TTG GAC AGC      528
Val Gln Lys Thr Val Thr Ala Ile Lys Thr Ile Val Ile Leu Asp Ser
                 165                 170                 175

AAA GTG GAT TAT AGA GGT TAT CAA TCC ATG GAC AAC TTT ATT AAA AAA      576
Lys Val Asp Tyr Arg Gly Tyr Gln Ser Met Asp Asn Phe Ile Lys Lys
             180                 185                 190

AAC ACT CCA CAA GGT TTC AAA GGA TCA AGT TTT AAA ACT GTA GAA GTT      624
Asn Thr Pro Gln Gly Phe Lys Gly Ser Ser Phe Lys Thr Val Glu Val
         195                 200                 205

AAC CGC AAA GAA CAA GTT GCT CTT ATA ATG AAC TCT TCG GGT TCA ACC      672
Asn Arg Lys Glu Gln Val Ala Leu Ile Met Asn Ser Ser Gly Ser Thr
     210                 215                 220
```

```
GGT  TTG  CCA  AAA  GGT  GTG  CAA  CTT  ACT  CAT  GAA  AAT  TTG  GTC  ACG  CGT      720
Gly  Leu  Pro  Lys  Gly  Val  Gln  Leu  Thr  His  Glu  Asn  Leu  Val  Thr  Arg
225            230                      235                      240

TTT  TCT  CAC  GCT  AGA  GAT  CCA  ATT  TAT  GGA  AAC  CAA  GTT  TCA  CCA  GGC      768
Phe  Ser  His  Ala  Arg  Asp  Pro  Ile  Tyr  Gly  Asn  Gln  Val  Ser  Pro  Gly
                    245                      250                      255

ACG  GCT  ATT  TTA  ACT  GTA  GTA  CCA  TTC  CAT  CAT  GGT  TTT  GGT  ATG  TTT      816
Thr  Ala  Ile  Leu  Thr  Val  Val  Pro  Phe  His  His  Gly  Phe  Gly  Met  Phe
               260                      265                      270

ACT  ACT  TTA  GGC  TAT  CTA  ACT  TGT  GGT  TTT  CGT  ATT  GTC  ATG  TTA  ACG      864
Thr  Thr  Leu  Gly  Tyr  Leu  Thr  Cys  Gly  Phe  Arg  Ile  Val  Met  Leu  Thr
          275                      280                      285

AAA  TTT  GAC  GAA  GAG  ACT  TTT  TTA  AAA  ACA  CTG  CAA  GAT  TAC  AAA  TGT      912
Lys  Phe  Asp  Glu  Glu  Thr  Phe  Leu  Lys  Thr  Leu  Gln  Asp  Tyr  Lys  Cys
     290                      295                      300

TCA  AGC  GTT  ATT  CTT  GTA  CCG  ACT  TTG  TTT  GCA  ATT  CTT  AAT  AGA  AGT      960
Ser  Ser  Val  Ile  Leu  Val  Pro  Thr  Leu  Phe  Ala  Ile  Leu  Asn  Arg  Ser
305                      310                      315                      320

GAA  TTA  CTC  GAT  AAA  TAT  GAT  TTA  TCA  AAT  TTA  GTT  GAA  ATT  GCA  TCT     1008
Glu  Leu  Leu  Asp  Lys  Tyr  Asp  Leu  Ser  Asn  Leu  Val  Glu  Ile  Ala  Ser
                    325                      330                      335

GGC  GGA  GCA  CCT  TTA  TCT  AAA  GAA  ATT  GGT  GAA  GCT  GTT  GCT  AGA  CGT     1056
Gly  Gly  Ala  Pro  Leu  Ser  Lys  Glu  Ile  Gly  Glu  Ala  Val  Ala  Arg  Arg
               340                      345                      350

TTT  AAT  TTA  CCG  GGT  GTT  CGT  CAA  GGC  TAT  GGT  TTA  ACA  GAA  ACA  ACC     1104
Phe  Asn  Leu  Pro  Gly  Val  Arg  Gln  Gly  Tyr  Gly  Leu  Thr  Glu  Thr  Thr
          355                      360                      365

TCT  GCA  ATT  ATT  ATC  ACA  CCG  GAA  GGC  GAT  GAT  AAA  CCA  GGT  GCT  TCT     1152
Ser  Ala  Ile  Ile  Ile  Thr  Pro  Glu  Gly  Asp  Asp  Lys  Pro  Gly  Ala  Ser
     370                      375                      380

GGC  AAA  GTT  GTG  CCA  TTA  TTT  AAA  GCA  AAA  GTT  ATC  GAT  CTT  GAT  ACT     1200
Gly  Lys  Val  Val  Pro  Leu  Phe  Lys  Ala  Lys  Val  Ile  Asp  Leu  Asp  Thr
385                      390                      395                      400

AAA  AAA  ACT  TTG  GGC  CCG  AAC  AGA  CGT  GGA  GAA  GTT  TGT  GTA  AAG  GGT     1248
Lys  Lys  Thr  Leu  Gly  Pro  Asn  Arg  Arg  Gly  Glu  Val  Cys  Val  Lys  Gly
                    405                      410                      415

CCT  ATG  CTT  ATG  AAA  GGT  TAT  GTA  GAT  AAT  CCA  GAA  GCA  ACA  AGA  GAA     1296
Pro  Met  Leu  Met  Lys  Gly  Tyr  Val  Asp  Asn  Pro  Glu  Ala  Thr  Arg  Glu
               420                      425                      430

ATC  ATA  GAT  GAA  GAA  GGT  TGG  TTG  CAC  ACA  GGA  GAT  ATT  GGG  TAT  TAC     1344
Ile  Ile  Asp  Glu  Glu  Gly  Trp  Leu  His  Thr  Gly  Asp  Ile  Gly  Tyr  Tyr
          435                      440                      445

GAT  GAA  GAA  AAA  CAT  TTC  TTT  ATC  GTG  GAT  CGT  TTG  AAG  TCT  TTA  ATC     1392
Asp  Glu  Glu  Lys  His  Phe  Phe  Ile  Val  Asp  Arg  Leu  Lys  Ser  Leu  Ile
     450                      455                      460

AAA  TAC  AAA  GGA  TAT  CAA  GTA  CCA  CCT  GCT  GAA  TTA  GAA  TCT  GTT  CTT     1440
Lys  Tyr  Lys  Gly  Tyr  Gln  Val  Pro  Pro  Ala  Glu  Leu  Glu  Ser  Val  Leu
465                      470                      475                      480

TTG  CAA  CAT  CCA  AAT  ATT  TTT  GAT  GCC  GGC  GTT  GCT  GGC  GTT  CCA  GAT     1488
Leu  Gln  His  Pro  Asn  Ile  Phe  Asp  Ala  Gly  Val  Ala  Gly  Val  Pro  Asp
                    485                      490                      495

CCT  ATA  GCT  GGT  GAG  CTT  CCG  GGA  GCT  GTT  GTT  GTA  CTT  GAA  AAA  GGA     1536
Pro  Ile  Ala  Gly  Glu  Leu  Pro  Gly  Ala  Val  Val  Val  Leu  Glu  Lys  Gly
               500                      505                      510

AAA  TCT  ATG  ACT  GAA  AAA  GAA  GTA  ATG  GAT  TAC  GTT  GCT  AGT  CAA  GTT     1584
Lys  Ser  Met  Thr  Glu  Lys  Glu  Val  Met  Asp  Tyr  Val  Ala  Ser  Gln  Val
          515                      520                      525

TCA  AAT  GCA  AAA  CGT  TTG  CGT  GGT  GGT  GTC  CGT  TTT  GTG  GAC  GAA  GTA     1632
Ser  Asn  Ala  Lys  Arg  Leu  Arg  Gly  Gly  Val  Arg  Phe  Val  Asp  Glu  Val
     530                      535                      540
```

```
CCT  AAA  GGT  CTC  ACT  GGT  AAA  ATT  GAC  GGT  AAA  GCA  ATT  AGA  GAA  ATA    1680
Pro  Lys  Gly  Leu  Thr  Gly  Lys  Ile  Asp  Gly  Lys  Ala  Ile  Arg  Glu  Ile
545                      550                      555                      560

CTG  AAG  AAA  CCA  GTT  GCT  AAG  ATG                                            1704
Leu  Lys  Lys  Pro  Val  Ala  Lys  Met
                    565
```

(2) INFORMATION FOR SEQ ID NO:6:

(i) SEQUENCE CHARACTERISTICS:
        (A) LENGTH: 568 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ala  Phe  Ser  Leu  Arg  Ser  Ile  Leu  Glu  Ala  Gln  Lys  Met  Glu  Leu
 1              5                        10                       15

Arg  Asn  Thr  Pro  Gly  Gly  Ser  Leu  Glu  Asn  Asp  Glu  Asn  Ile  Val  Tyr
               20                       25                       30

Gly  Pro  Glu  Pro  Phe  Tyr  Pro  Ile  Glu  Glu  Gly  Ser  Ala  Gly  Ala  Gln
               35                  40                       45

Leu  Arg  Lys  Tyr  Met  Asp  Arg  Tyr  Ala  Lys  Leu  Gly  Ala  Ile  Ala  Phe
 50                            55                            60

Thr  Asn  Ala  Leu  Thr  Gly  Val  Asp  Tyr  Thr  Tyr  Ala  Glu  Tyr  Leu  Glu
 65                       70                       75                       80

Lys  Ser  Cys  Cys  Leu  Gly  Glu  Ala  Leu  Lys  Asn  Tyr  Gly  Leu  Val  Val
                    85                       90                       95

Asp  Gly  Arg  Ile  Ala  Leu  Cys  Ser  Glu  Asn  Cys  Glu  Glu  Phe  Phe  Ile
               100                      105                      110

Pro  Val  Leu  Ala  Gly  Leu  Phe  Ile  Gly  Val  Gly  Val  Ala  Pro  Thr  Asn
               115                      120                      125

Glu  Ile  Tyr  Thr  Leu  Arg  Glu  Leu  Val  His  Ser  Leu  Gly  Ile  Ser  Lys
               130                      135                      140

Pro  Thr  Ile  Val  Phe  Ser  Ser  Lys  Lys  Gly  Leu  Asp  Lys  Val  Ile  Thr
145                      150                      155                      160

Val  Gln  Lys  Thr  Val  Thr  Ala  Ile  Lys  Thr  Ile  Val  Ile  Leu  Asp  Ser
               165                      170                      175

Lys  Val  Asp  Tyr  Arg  Gly  Tyr  Gln  Ser  Met  Asp  Asn  Phe  Ile  Lys  Lys
               180                      185                      190

Asn  Thr  Pro  Gln  Gly  Phe  Lys  Gly  Ser  Ser  Phe  Lys  Thr  Val  Glu  Val
               195                      200                      205

Asn  Arg  Lys  Glu  Gln  Val  Ala  Leu  Ile  Met  Asn  Ser  Ser  Gly  Ser  Thr
          210                      215                      220

Gly  Leu  Pro  Lys  Gly  Val  Gln  Leu  Thr  His  Glu  Asn  Leu  Val  Thr  Arg
225                      230                      235                      240

Phe  Ser  His  Ala  Arg  Asp  Pro  Ile  Tyr  Gly  Asn  Gln  Val  Ser  Pro  Gly
                    245                      250                      255

Thr  Ala  Ile  Leu  Thr  Val  Val  Pro  Phe  His  His  Gly  Phe  Gly  Met  Phe
               260                      265                      270

Thr  Thr  Leu  Gly  Tyr  Leu  Thr  Cys  Gly  Phe  Arg  Ile  Val  Met  Leu  Thr
          275                      280                      285

Lys  Phe  Asp  Glu  Glu  Thr  Phe  Leu  Lys  Thr  Leu  Gln  Asp  Tyr  Lys  Cys
          290                      295                      300

Ser  Ser  Val  Ile  Leu  Val  Pro  Thr  Leu  Phe  Ala  Ile  Leu  Asn  Arg  Ser
305                      310                      315                      320
```

| Glu | Leu | Leu | Asp | Lys | Tyr | Asp | Leu | Ser | Asn | Leu | Val | Glu | Ile | Ala | Ser |
|||| |325| |||| 330 |||||335||

| Gly | Gly | Ala | Pro | Leu | Ser | Lys | Glu | Ile | Gly | Glu | Ala | Val | Ala | Arg | Arg |
|||| 340 |||| 345 |||| 350 |||

| Phe | Asn | Leu | Pro | Gly | Val | Arg | Gln | Gly | Tyr | Gly | Leu | Thr | Glu | Thr | Thr |
|||| 355 |||| 360 |||| 365 |||

| Ser | Ala | Ile | Ile | Ile | Thr | Pro | Glu | Gly | Asp | Asp | Lys | Pro | Gly | Ala | Ser |
|| 370 |||||| 375 |||| 380 |||

| Gly | Lys | Val | Val | Pro | Leu | Phe | Lys | Ala | Lys | Val | Ile | Asp | Leu | Asp | Thr |
| 385 ||||| 390 |||| 395 |||||400|

| Lys | Lys | Thr | Leu | Gly | Pro | Asn | Arg | Arg | Gly | Glu | Val | Cys | Val | Lys | Gly |
||||| 405 |||| 410 |||| 415 ||

| Pro | Met | Leu | Met | Lys | Gly | Tyr | Val | Asp | Asn | Pro | Glu | Ala | Thr | Arg | Glu |
|||| 420 |||| 425 |||| 430 ||

| Ile | Ile | Asp | Glu | Glu | Gly | Trp | Leu | His | Thr | Gly | Asp | Ile | Gly | Tyr | Tyr |
||| 435 |||| 440 |||| 445 |||

| Asp | Glu | Glu | Lys | His | Phe | Phe | Ile | Val | Asp | Arg | Leu | Lys | Ser | Leu | Ile |
|| 450 |||| 455 |||| 460 ||||

| Lys | Tyr | Lys | Gly | Tyr | Gln | Val | Pro | Pro | Ala | Glu | Leu | Glu | Ser | Val | Leu |
| 465 |||| 470 |||| 475 |||||480|

| Leu | Gln | His | Pro | Asn | Ile | Phe | Asp | Ala | Gly | Val | Ala | Gly | Val | Pro | Asp |
|||| 485 |||| 490 |||| 495 ||

| Pro | Ile | Ala | Gly | Glu | Leu | Pro | Gly | Ala | Val | Val | Val | Leu | Glu | Lys | Gly |
|||| 500 |||| 505 |||| 510 ||

| Lys | Ser | Met | Thr | Glu | Lys | Glu | Val | Met | Asp | Tyr | Val | Ala | Ser | Gln | Val |
||| 515 |||| 520 |||| 525 |||

| Ser | Asn | Ala | Lys | Arg | Leu | Arg | Gly | Gly | Val | Arg | Phe | Val | Asp | Glu | Val |
|| 530 |||| 535 |||| 540 ||||

| Pro | Lys | Gly | Leu | Thr | Gly | Lys | Ile | Asp | Gly | Lys | Ala | Ile | Arg | Glu | Ile |
| 545 ||||| 550 |||| 555 |||||560|

| Leu | Lys | Lys | Pro | Val | Ala | Lys | Met |
||||| 565 |||

(2) INFORMATION FOR SEQ ID NO:7:

(i) SEQUENCE CHARACTERISTICS:
        (A) LENGTH: 87 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: E. coli (ix) FEATURE:
        (A) NAME/KEY: Modified-site
        (B) LOCATION: 53
        (D) OTHER INFORMATION: /product="Lys-53"
            / note= "Lys-53 is biotinylated by the action of biotin
            holoenzyme synthetase"

(xi) SEQUENCE DESCRIPTION: SEQ ID NO:7:

| Met | Glu | Ala | Pro | Ala | Ala | Ala | Glu | Ile | Ser | Gly | His | Ile | Val | Arg | Ser |
| 1 |||| 5 |||| 10 |||| 15 ||

| Pro | Met | Val | Gly | Thr | Phe | Tyr | Arg | Thr | Pro | Ser | Pro | Asp | Ala | Lys | Ala |
|||| 20 |||| 25 |||| 30 ||

| Phe | Ile | Glu | Val | Gly | Gln | Lys | Val | Asn | Val | Gly | Asp | Thr | Leu | Cys | Ile |
||| 35 |||| 40 |||| 45 |||

|     |     |     |     |     |     |     |     |     |     |     |     |     |     |     |     |
|---|---|---|---|---|---|---|---|---|---|---|---|---|---|---|---|
| Val | Glu | Ala | Met | Lys | Met | Met | Asn | Gln | Ile | Glu | Ala | Asp | Lys | Ser | Gly |
|     | 50  |     |     |     |     | 55  |     |     |     |     | 60  |     |     |     |     |
| Thr | Val | Lys | Ala | Ile | Leu | Val | Glu | Ser | Gly | Gln | Pro | Val | Glu | Phe | Asp |
| 65  |     |     |     |     | 70  |     |     |     |     | 75  |     |     |     |     | 80  |
| Glu | Pro | Leu | Val | Val | Ile | Glu |     |     |     |     |     |     |     |     |     |
|     |     |     |     | 85  |     |     |     |     |     |     |     |     |     |     |     |

( 2 ) INFORMATION FOR SEQ ID NO:8:

( i ) SEQUENCE CHARACTERISTICS:
        ( A ) LENGTH: 1908 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 1..1908
        ( D ) OTHER INFORMATION: /note= "The nucleotide sequence of
            the biotinylated firefly luciferase gene contained in
            recombinant plasmid pHLf248 DNA"

( i x ) FEATURE:
        ( A ) NAME/KEY: CDS
        ( B ) LOCATION: 1..1908

( x i ) SEQUENCE DESCRIPTION: SEQ ID NO:8:

| ATG | GAA | AAC | ATG | GAG | AAC | GAT | GAA | AAT | ATT | GTG | TAT | GGT | CCT | GAA | CCA | 48 |
|---|---|---|---|---|---|---|---|---|---|---|---|---|---|---|---|---|
| Met | Glu | Asn | Met | Glu | Asn | Asp | Glu | Asn | Ile | Val | Tyr | Gly | Pro | Glu | Pro |  |
| 570 |  |  |  |  | 575 |  |  |  |  | 580 |  |  |  |  |  |  |
| TTT | TAC | CCT | ATT | GAA | GAG | GGA | TCT | GCT | GGA | GCA | CAA | TTG | CGC | AAG | TAT | 96 |
| Phe | Tyr | Pro | Ile | Glu | Glu | Gly | Ser | Ala | Gly | Ala | Gln | Leu | Arg | Lys | Tyr |  |
| 585 |  |  |  |  | 590 |  |  |  |  | 595 |  |  |  |  | 600 |  |
| ATG | GAT | CGA | TAT | GCA | AAA | CTT | GGA | GCA | ATT | GCT | TTT | ACT | AAC | GCA | CTT | 144 |
| Met | Asp | Arg | Tyr | Ala | Lys | Leu | Gly | Ala | Ile | Ala | Phe | Thr | Asn | Ala | Leu |  |
|  |  |  |  | 605 |  |  |  |  | 610 |  |  |  |  | 615 |  |  |
| ACC | GGT | GTC | GAT | TAT | ACG | TAC | GCC | GAA | TAC | TTA | GAA | AAA | TCA | TGC | TGT | 192 |
| Thr | Gly | Val | Asp | Tyr | Thr | Tyr | Ala | Glu | Tyr | Leu | Glu | Lys | Ser | Cys | Cys |  |
|  |  |  | 620 |  |  |  |  | 625 |  |  |  |  | 630 |  |  |  |
| CTA | GGA | GAG | GCT | TTA | AAG | AAT | TAT | GGT | TTG | GTT | GTT | GAT | GGA | AGA | ATT | 240 |
| Leu | Gly | Glu | Ala | Leu | Lys | Asn | Tyr | Gly | Leu | Val | Val | Asp | Gly | Arg | Ile |  |
|  |  | 635 |  |  |  |  | 640 |  |  |  |  | 645 |  |  |  |  |
| GCG | TTA | TGC | AGT | GAA | AAC | TGT | GAA | GAG | TTC | TTT | ATT | CCT | GTA | TTA | GCC | 288 |
| Ala | Leu | Cys | Ser | Glu | Asn | Cys | Glu | Glu | Phe | Phe | Ile | Pro | Val | Leu | Ala |  |
|  | 650 |  |  |  |  | 655 |  |  |  |  | 660 |  |  |  |  |  |
| GGT | TTA | TTT | ATA | GGT | GTC | GGT | GTG | GCT | CCA | ACT | AAT | GAG | ATT | TAC | ACT | 336 |
| Gly | Leu | Phe | Ile | Gly | Val | Gly | Val | Ala | Pro | Thr | Asn | Glu | Ile | Tyr | Thr |  |
| 665 |  |  |  |  | 670 |  |  |  |  | 675 |  |  |  |  | 680 |  |
| CTA | CGT | GAA | TTG | GTT | CAC | AGT | TTA | GGC | ATC | TCT | AAG | CCA | ACA | ATT | GTA | 384 |
| Leu | Arg | Glu | Leu | Val | His | Ser | Leu | Gly | Ile | Ser | Lys | Pro | Thr | Ile | Val |  |
|  |  |  |  | 685 |  |  |  |  | 690 |  |  |  |  | 695 |  |  |
| TTT | AGT | TCT | AAA | AAA | GGA | TTA | GAT | AAA | GTT | ATA | ACT | GTA | CAA | AAA | ACG | 432 |
| Phe | Ser | Ser | Lys | Lys | Gly | Leu | Asp | Lys | Val | Ile | Thr | Val | Gln | Lys | Thr |  |
|  |  |  | 700 |  |  |  |  | 705 |  |  |  |  | 710 |  |  |  |
| GTA | ACT | GCT | ATT | AAA | ACC | ATT | GTT | ATA | TTG | GAC | AGC | AAA | GTG | GAT | TAT | 480 |
| Val | Thr | Ala | Ile | Lys | Thr | Ile | Val | Ile | Leu | Asp | Ser | Lys | Val | Asp | Tyr |  |
|  |  | 715 |  |  |  |  | 720 |  |  |  |  | 725 |  |  |  |  |
| AGA | GGT | TAT | CAA | TCC | ATG | GAC | AAC | TTT | ATT | AAA | AAA | AAC | ACT | CCA | CAA | 528 |
| Arg | Gly | Tyr | Gln | Ser | Met | Asp | Asn | Phe | Ile | Lys | Lys | Asn | Thr | Pro | Gln |  |
|  | 730 |  |  |  |  | 735 |  |  |  |  | 740 |  |  |  |  |  |
| GGT | TTC | AAA | GGA | TCA | AGT | TTT | AAA | ACT | GTA | GAA | GTT | AAC | CGC | AAA | GAA | 576 |
| Gly | Phe | Lys | Gly | Ser | Ser | Phe | Lys | Thr | Val | Glu | Val | Asn | Arg | Lys | Glu |  |

```
                745                        750                        755                       760

CAA  GTT  GCT  CTT  ATA  ATG  AAC  TCT  TCG  GGT  TCA  ACC  GGT  TTG  CCA  AAA           624
Gln  Val  Ala  Leu  Ile  Met  Asn  Ser  Ser  Gly  Ser  Thr  Gly  Leu  Pro  Lys
                    765                   770                             775

GGT  GTG  CAA  CTT  ACT  CAT  GAA  AAT  TTG  GTC  ACG  CGT  TTT  TCT  CAC  GCT           672
Gly  Val  Gln  Leu  Thr  His  Glu  Asn  Leu  Val  Thr  Arg  Phe  Ser  His  Ala
               780                        785                             790

AGA  GAT  CCA  ATT  TAT  GGA  AAC  CAA  GTT  TCA  CCA  GGC  ACG  GCT  ATT  TTA           720
Arg  Asp  Pro  Ile  Tyr  Gly  Asn  Gln  Val  Ser  Pro  Gly  Thr  Ala  Ile  Leu
          795                             800                   805

ACT  GTA  GTA  CCA  TTC  CAT  CAT  GGT  TTT  GGT  ATG  TTT  ACT  ACT  TTA  GGC           768
Thr  Val  Val  Pro  Phe  His  His  Gly  Phe  Gly  Met  Phe  Thr  Thr  Leu  Gly
     810                             815                   820

TAT  CTA  ACT  TGT  GGT  TTT  CGT  ATT  GTC  ATG  TTA  ACG  AAA  TTT  GAC  GAA           816
Tyr  Leu  Thr  Cys  Gly  Phe  Arg  Ile  Val  Met  Leu  Thr  Lys  Phe  Asp  Glu
825                       830                   835                            840

GAG  ACT  TTT  TTA  AAA  ACA  CTG  CAA  GAT  TAC  AAA  TGT  TCA  AGC  GTT  ATT           864
Glu  Thr  Phe  Leu  Lys  Thr  Leu  Gln  Asp  Tyr  Lys  Cys  Ser  Ser  Val  Ile
                    845                   850                        855

CTT  GTA  CCG  ACT  TTG  TTT  GCA  ATT  CTT  AAT  AGA  AGT  GAA  TTA  CTC  GAT           912
Leu  Val  Pro  Thr  Leu  Phe  Ala  Ile  Leu  Asn  Arg  Ser  Glu  Leu  Leu  Asp
               860                        865                        870

AAA  TAT  GAT  TTA  TCA  AAT  TTA  GTT  GAA  ATT  GCA  TCT  GGC  GGA  GCA  CCT           960
Lys  Tyr  Asp  Leu  Ser  Asn  Leu  Val  Glu  Ile  Ala  Ser  Gly  Gly  Ala  Pro
          875                             880                   885

TTA  TCT  AAA  GAA  ATT  GGT  GAA  GCT  GTT  GCT  AGA  CGT  TTT  AAT  TTA  CCG          1008
Leu  Ser  Lys  Glu  Ile  Gly  Glu  Ala  Val  Ala  Arg  Arg  Phe  Asn  Leu  Pro
     890                             895                   900

GGT  GTT  CGT  CAA  GGC  TAT  GGT  TTA  ACA  GAA  ACA  ACC  TCT  GCA  ATT  ATT          1056
Gly  Val  Arg  Gln  Gly  Tyr  Gly  Leu  Thr  Glu  Thr  Thr  Ser  Ala  Ile  Ile
905                       910                  915                             920

ATC  ACA  CCG  GAA  GGC  GAT  GAT  AAA  CCA  GGT  GCT  TCT  GGC  AAA  GTT  GTG          1104
Ile  Thr  Pro  Glu  Gly  Asp  Asp  Lys  Pro  Gly  Ala  Ser  Gly  Lys  Val  Val
                    925                   930                        935

CCA  TTA  TTT  AAA  GCA  AAA  GTT  ATC  GAT  CTT  GAT  ACT  AAA  AAA  ACT  TTG          1152
Pro  Leu  Phe  Lys  Ala  Lys  Val  Ile  Asp  Leu  Asp  Thr  Lys  Lys  Thr  Leu
               940                        945                        950

GGC  CCG  AAC  AGA  CGT  GGA  GAA  GTT  TGT  GTA  AAG  GGT  CCT  ATG  CTT  ATG          1200
Gly  Pro  Asn  Arg  Arg  Gly  Glu  Val  Cys  Val  Lys  Gly  Pro  Met  Leu  Met
          955                             960                   965

AAA  GGT  TAT  GTA  GAT  AAT  CCA  GAA  GCA  ACA  AGA  GAA  ATA  ATA  GAT  GAA          1248
Lys  Gly  Tyr  Val  Asp  Asn  Pro  Glu  Ala  Thr  Arg  Glu  Ile  Ile  Asp  Glu
     970                             975                   980

GAA  GGT  TGG  TTG  CAC  ACA  GGA  GAT  ATT  GGG  TAT  TAC  GAT  GAA  GAA  AAA          1296
Glu  Gly  Trp  Leu  His  Thr  Gly  Asp  Ile  Gly  Tyr  Tyr  Asp  Glu  Glu  Lys
985                       990                  995                            1000

CAT  TTC  TTT  ATC  GTG  GAT  CGT  TTG  AAG  TCT  TTA  ATC  AAA  TAC  AAA  GGA          1344
His  Phe  Phe  Ile  Val  Asp  Arg  Leu  Lys  Ser  Leu  Ile  Lys  Tyr  Lys  Gly
                    1005                  1010                       1015

TAT  CAA  GTA  CCA  CCT  GCT  GAA  TTA  GAA  TCT  GTT  CTT  TTG  CAA  CAT  CCA          1392
Tyr  Gln  Val  Pro  Pro  Ala  Glu  Leu  Glu  Ser  Val  Leu  Leu  Gln  His  Pro
               1020                       1025                       1030

AAT  ATT  TTT  GAT  GCC  GGC  GTT  GCT  GGC  GTT  CCA  GAT  CCT  ATA  GCT  GGT          1440
Asn  Ile  Phe  Asp  Ala  Gly  Val  Ala  Gly  Val  Pro  Asp  Pro  Ile  Ala  Gly
          1035                            1040                  1045

GAG  CTT  CCG  GGA  GCT  GTT  GTT  GTA  CTT  GAA  AAA  GGA  AAA  TCT  ATG  ACT          1488
Glu  Leu  Pro  Gly  Ala  Val  Val  Val  Leu  Glu  Lys  Gly  Lys  Ser  Met  Thr
     1050                            1055                  1060

GAA  AAA  GAA  GTA  ATG  GAT  TAC  GTT  GCT  AGT  CAA  GTT  TCA  AAT  GCA  AAA          1536
Glu  Lys  Glu  Val  Met  Asp  Tyr  Val  Ala  Ser  Gln  Val  Ser  Asn  Ala  Lys
```

|  |  |  |  |  |  |  |  |  |  |  |  |  |  |  |  |
|---|---|---|---|---|---|---|---|---|---|---|---|---|---|---|---|
| 1065 | | | | | 1070 | | | | | 1075 | | | | | 1080 |
| CGT | TTG | CGT | GGT | GGT | GTC | CGT | TTT | GTG | GAC | GAA | GTA | CCT | AAA | GGT | CTC | 1584 |
| Arg | Leu | Arg | Gly | Gly | Val | Arg | Phe | Val | Asp | Glu | Val | Pro | Lys | Gly | Leu | |
| | | | | 1085 | | | | | 1090 | | | | | 1095 | | |
| ACT | GGT | AAA | ATT | GAC | GGT | AAA | GCA | ATT | AGA | GAA | ATA | CTG | AAG | AAA | CCA | 1632 |
| Thr | Gly | Lys | Ile | Asp | Gly | Lys | Ala | Ile | Arg | Glu | Ile | Leu | Lys | Lys | Pro | |
| | | | | 1100 | | | | | 1105 | | | | | 1110 | | |
| GTT | GCT | AAG | GGA | TCC | ATG | GAA | GCG | CCA | GCA | GCA | GCG | GAA | ATC | AGT | GGT | 1680 |
| Val | Ala | Lys | Gly | Ser | Met | Glu | Ala | Pro | Ala | Ala | Ala | Glu | Ile | Ser | Gly | |
| | | | | 1115 | | | | | 1120 | | | | | 1125 | | |
| CAC | ATC | GTA | CGT | TCC | CCG | ATG | GTT | GGT | ACT | TTC | TAC | CGC | ACC | CCA | AGC | 1728 |
| His | Ile | Val | Arg | Ser | Pro | Met | Val | Gly | Thr | Phe | Tyr | Arg | Thr | Pro | Ser | |
| | | | | 1130 | | | | | 1135 | | | | | 1140 | | |
| CCG | GAC | GCA | AAA | GCG | TTC | ATC | GAA | GTG | GGT | CAG | AAA | GTC | AAC | GTG | GGC | 1776 |
| Pro | Asp | Ala | Lys | Ala | Phe | Ile | Glu | Val | Gly | Gln | Lys | Val | Asn | Val | Gly | |
| 1145 | | | | | 1150 | | | | | 1155 | | | | | 1160 | |
| GAT | ACC | CTG | TGC | ATC | GTT | GAA | GCC | ATG | AAA | ATG | ATG | AAC | CAG | ATC | GAA | 1824 |
| Asp | Thr | Leu | Cys | Ile | Val | Glu | Ala | Met | Lys | Met | Met | Asn | Gln | Ile | Glu | |
| | | | | 1165 | | | | | 1170 | | | | | 1175 | | |
| GCG | GAC | AAA | TCC | GGT | ACC | GTG | AAA | GCA | ATT | CTG | GTC | GAA | AGT | GGA | CAA | 1872 |
| Ala | Asp | Lys | Ser | Gly | Thr | Val | Lys | Ala | Ile | Leu | Val | Glu | Ser | Gly | Gln | |
| | | | | 1180 | | | | | 1185 | | | | | 1190 | | |
| CCG | GTA | GAA | TTT | GAC | GAG | CCG | CTG | GTC | GTC | ATC | GAG | | | | | 1908 |
| Pro | Val | Glu | Phe | Asp | Glu | Pro | Leu | Val | Val | Ile | Glu | | | | | |
| | | | | 1195 | | | | | 1200 | | | | | | | |

(2) INFORMATION FOR SEQ ID NO:9:

(i) SEQUENCE CHARACTERISTICS:
        (A) LENGTH: 636 amino acids
        (B) TYPE: amino acid
        (D) TOPOLOGY: linear (ii) MOLECULE TYPE: protein (xi) SEQUENCE DESCRIPTION: SEQ ID NO:9:

| Met | Glu | Asn | Met | Glu | Asn | Asp | Glu | Asn | Ile | Val | Tyr | Gly | Pro | Glu | Pro |
|---|---|---|---|---|---|---|---|---|---|---|---|---|---|---|---|
| 1 | | | | 5 | | | | | 10 | | | | | 15 | |
| Phe | Tyr | Pro | Ile | Glu | Glu | Gly | Ser | Ala | Gly | Ala | Gln | Leu | Arg | Lys | Tyr |
| | | | 20 | | | | | 25 | | | | | 30 | | |
| Met | Asp | Arg | Tyr | Ala | Lys | Leu | Gly | Ala | Ile | Ala | Phe | Thr | Asn | Ala | Leu |
| | | 35 | | | | | 40 | | | | | 45 | | | |
| Thr | Gly | Val | Asp | Tyr | Thr | Tyr | Ala | Glu | Tyr | Leu | Glu | Lys | Ser | Cys | Cys |
| | 50 | | | | | 55 | | | | | 60 | | | | |
| Leu | Gly | Glu | Ala | Leu | Lys | Asn | Tyr | Gly | Leu | Val | Val | Asp | Gly | Arg | Ile |
| 65 | | | | | 70 | | | | | 75 | | | | | 80 |
| Ala | Leu | Cys | Ser | Glu | Asn | Cys | Glu | Glu | Phe | Phe | Ile | Pro | Val | Leu | Ala |
| | | | | 85 | | | | | 90 | | | | | 95 | |
| Gly | Leu | Phe | Ile | Gly | Val | Gly | Val | Ala | Pro | Thr | Asn | Glu | Ile | Tyr | Thr |
| | | | 100 | | | | | 105 | | | | | 110 | | |
| Leu | Arg | Glu | Leu | Val | His | Ser | Leu | Gly | Ile | Ser | Lys | Pro | Thr | Ile | Val |
| | | 115 | | | | | 120 | | | | | 125 | | | |
| Phe | Ser | Ser | Lys | Lys | Gly | Leu | Asp | Lys | Val | Ile | Thr | Val | Gln | Lys | Thr |
| | | 130 | | | | | 135 | | | | | 140 | | | |
| Val | Thr | Ala | Ile | Lys | Thr | Ile | Val | Ile | Leu | Asp | Ser | Lys | Val | Asp | Tyr |
| 145 | | | | | 150 | | | | | 155 | | | | | 160 |
| Arg | Gly | Tyr | Gln | Ser | Met | Asp | Asn | Phe | Ile | Lys | Lys | Asn | Thr | Pro | Gln |
| | | | | 165 | | | | | 170 | | | | | 175 | |
| Gly | Phe | Lys | Gly | Ser | Ser | Phe | Lys | Thr | Val | Glu | Val | Asn | Arg | Lys | Glu |

|     |     |     |     |     |     |     |     |     |     |     |     |     |     |     |
|---|---|---|---|---|---|---|---|---|---|---|---|---|---|---|
|     |     |     |     |     | 180 |     |     |     |     | 185 |     |     |     | 190 |
| Gln | Val | Ala | Leu | Ile | Met | Asn | Ser | Ser | Gly | Ser | Thr | Gly | Leu | Pro | Lys |
|     |     |     | 195 |     |     |     | 200 |     |     |     |     | 205 |     |     |     |
| Gly | Val | Gln | Leu | Thr | His | Glu | Asn | Leu | Val | Thr | Arg | Phe | Ser | His | Ala |
|     |     | 210 |     |     |     | 215 |     |     |     |     | 220 |     |     |     |     |
| Arg | Asp | Pro | Ile | Tyr | Gly | Asn | Gln | Val | Ser | Pro | Gly | Thr | Ala | Ile | Leu |
| 225 |     |     |     |     | 230 |     |     |     |     | 235 |     |     |     |     | 240 |
| Thr | Val | Val | Pro | Phe | His | His | Gly | Phe | Met | Phe | Thr | Thr | Leu | Gly |
|     |     |     |     | 245 |     |     |     |     | 250 |     |     |     |     | 255 |
| Tyr | Leu | Thr | Cys | Gly | Phe | Arg | Ile | Val | Met | Leu | Thr | Lys | Phe | Asp | Glu |
|     |     |     | 260 |     |     |     |     | 265 |     |     |     |     | 270 |     |     |
| Glu | Thr | Phe | Leu | Lys | Thr | Leu | Gln | Asp | Tyr | Lys | Cys | Ser | Ser | Val | Ile |
|     |     | 275 |     |     |     |     | 280 |     |     |     |     | 285 |     |     |     |
| Leu | Val | Pro | Thr | Leu | Phe | Ala | Ile | Leu | Asn | Arg | Ser | Glu | Leu | Leu | Asp |
|     | 290 |     |     |     |     | 295 |     |     |     |     | 300 |     |     |     |     |
| Lys | Tyr | Asp | Leu | Ser | Asn | Leu | Val | Glu | Ile | Ala | Ser | Gly | Gly | Ala | Pro |
| 305 |     |     |     |     | 310 |     |     |     |     | 315 |     |     |     |     | 320 |
| Leu | Ser | Lys | Glu | Ile | Gly | Glu | Ala | Val | Ala | Arg | Arg | Phe | Asn | Leu | Pro |
|     |     |     |     | 325 |     |     |     |     | 330 |     |     |     |     | 335 |     |
| Gly | Val | Arg | Gln | Gly | Tyr | Gly | Leu | Thr | Glu | Thr | Thr | Ser | Ala | Ile | Ile |
|     |     |     | 340 |     |     |     |     | 345 |     |     |     |     | 350 |     |     |
| Ile | Thr | Pro | Glu | Gly | Asp | Asp | Lys | Pro | Gly | Ala | Ser | Gly | Lys | Val | Val |
|     |     | 355 |     |     |     |     | 360 |     |     |     |     | 365 |     |     |     |
| Pro | Leu | Phe | Lys | Ala | Lys | Val | Ile | Asp | Leu | Asp | Thr | Lys | Lys | Thr | Leu |
|     | 370 |     |     |     |     | 375 |     |     |     |     | 380 |     |     |     |     |
| Gly | Pro | Asn | Arg | Arg | Gly | Glu | Val | Cys | Val | Lys | Gly | Pro | Met | Leu | Met |
| 385 |     |     |     |     | 390 |     |     |     |     | 395 |     |     |     |     | 400 |
| Lys | Gly | Tyr | Val | Asp | Asn | Pro | Glu | Ala | Thr | Arg | Glu | Ile | Ile | Asp | Glu |
|     |     |     |     | 405 |     |     |     |     | 410 |     |     |     |     | 415 |     |
| Glu | Gly | Trp | Leu | His | Thr | Gly | Asp | Ile | Gly | Tyr | Tyr | Asp | Glu | Glu | Lys |
|     |     |     | 420 |     |     |     |     | 425 |     |     |     |     | 430 |     |     |
| His | Phe | Phe | Ile | Val | Asp | Arg | Leu | Lys | Ser | Leu | Ile | Lys | Tyr | Lys | Gly |
|     |     | 435 |     |     |     |     | 440 |     |     |     |     | 445 |     |     |     |
| Tyr | Gln | Val | Pro | Pro | Ala | Glu | Leu | Glu | Ser | Val | Leu | Leu | Gln | His | Pro |
|     | 450 |     |     |     |     | 455 |     |     |     |     | 460 |     |     |     |     |
| Asn | Ile | Phe | Asp | Ala | Gly | Val | Ala | Gly | Val | Pro | Asp | Pro | Ile | Ala | Gly |
| 465 |     |     |     |     | 470 |     |     |     |     | 475 |     |     |     |     | 480 |
| Glu | Leu | Pro | Gly | Ala | Val | Val | Val | Leu | Glu | Lys | Gly | Lys | Ser | Met | Thr |
|     |     |     |     | 485 |     |     |     |     | 490 |     |     |     |     | 495 |     |
| Glu | Lys | Glu | Val | Met | Asp | Tyr | Val | Ala | Ser | Gln | Val | Ser | Asn | Ala | Lys |
|     |     |     | 500 |     |     |     |     | 505 |     |     |     |     | 510 |     |     |
| Arg | Leu | Arg | Gly | Gly | Val | Arg | Phe | Val | Asp | Glu | Val | Pro | Lys | Gly | Leu |
|     |     | 515 |     |     |     |     | 520 |     |     |     |     | 525 |     |     |     |
| Thr | Gly | Lys | Ile | Asp | Gly | Lys | Ala | Ile | Arg | Glu | Ile | Leu | Lys | Lys | Pro |
|     | 530 |     |     |     |     | 535 |     |     |     |     | 540 |     |     |     |     |
| Val | Ala | Lys | Gly | Ser | Met | Glu | Ala | Pro | Ala | Ala | Glu | Ile | Ser | Gly |
| 545 |     |     |     |     | 550 |     |     |     |     | 555 |     |     |     | 560 |
| His | Ile | Val | Arg | Ser | Pro | Met | Val | Gly | Thr | Phe | Tyr | Arg | Thr | Pro | Ser |
|     |     |     |     | 565 |     |     |     |     | 570 |     |     |     |     | 575 |     |
| Pro | Asp | Ala | Lys | Ala | Phe | Ile | Glu | Val | Gly | Gln | Lys | Val | Asn | Val | Gly |
|     |     |     | 580 |     |     |     |     | 585 |     |     |     |     | 590 |     |     |
| Asp | Thr | Leu | Cys | Ile | Val | Glu | Ala | Met | Lys | Met | Met | Asn | Gln | Ile | Glu |
|     |     | 595 |     |     |     |     | 600 |     |     |     |     | 605 |     |     |     |

```
Ala  Asp  Lys  Ser  Gly  Thr  Val  Lys  Ala  Ile  Leu  Val  Glu  Ser  Gly  Gln
     610                 615                      620
Pro  Val  Glu  Phe  Asp  Glu  Pro  Leu  Val  Val  Ile  Glu
625                      630                 635
```

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:10:

AGGAATAAAG AACTCTTCAC AGTT                                                                 2 4

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:11:

TTCATCGTTC TCGAGGTTTT CCATAGA                                                              2 7

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:12:

CCGGCGACCG TTGGATCCAT GGAAGCG                                                              2 7

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:13:

TTATCCAGCG GATCCACTAG TTTACTCGAT GACGACCAGC GG                                              4 2

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid -continued ( A ) DESCRIPTION: /desc = "Synthetic DNA"

( x i ) SEQUENCE DESCRIPTION: SEQ ID NO:14:

TGATTGACAT GGATCCCTTA GCAACT 26

BIOTINATED FIREFLY LUCIFERASE, A GENE FOR BIOTINATED FIREFLY LUCIFERASE, A RECOMBINANT DNA, A PROCESS FOR PRODUCING BIOTINATED LUCIFERASE AND A BIOLUMINESCENT ANALYSIS METHOD

FIELD OF THE INVENTION

The present invention relates to biotinated firefly luciferase, a gene for biotinated firefly luciferase, a recombinant DNA, a process for producing biotinated firefly luciferase and a bioluminescent analysis method using the biotinated firefly luciferase.

BACKGROUND OF THE INVENTION

Conventionally, immunoassays making use of chemically modified biotinated firefly luciferase still keeping 50% or more activity are known (Japanese Patent Application Laid-Open Publication No. 138463/1985).

However, none of the biotinated firefly luciferase of uniform properties can be obtained by chemical modification because the residue to which biotin is bound is not determinable and the number of biotin molecules bound to one luciferase molecule is not constant.

Hence, if firefly luciferase biotinated by chemical modification is employed in bioluminescent analysis, detection sensitivity is not satisfactory, and it is inappropriate to employ the biotinated firefly luciferase obtained by chemical modification in a bioluminescent analysis method where high sensitivity is required.

It is known that in cells biotin is bound by the action of biotin holoenzyme synthetase to biotin enzyme at a conserved Lys residue assumed to be one of the active centers of the enzyme [D. Samols et al., The Journal of Biological Chemistry, 263, 6461 (1988)].

Recently, the presence of a biotinated fusion protein was confirmed among fusion proteins between a target protein and a region containing the biotinated Lys residue of biotin enzyme which were produced by gene manipulation [J. E. Cronal, Jr., The Biological Chemistry, 265, 10327 (1990)].

Promega company produced biotinated firefly luciferase by the above method. That is, gene manipulation was used in their attempt to produce a fusion protein between luciferase derived from North American firefly (*Photinus pyralis*) and 12.5 kDa subunit of a transcarboxylase complex as biotin enzyme from *Proprionibacterium shermanii*. However, the resulting fusion protein was insoluble and little or no active biotinated firefly luciferase was obtained [a pamphlet of PinPoint Xa Protein Purification System available from Promega company].

SUMMARY OF THE INVENTION

Under such circumstances, the object of the present invention is to provide biotinated firefly luciferase free from the above drawbacks, a gene for the biotinated firefly luciferase, a process for producing the biotinated firefly luciferase and a bioluminescent analysis method using said luciferase.

The present invention relates to biotinated firefly luciferase, which comprises a biotinated peptide and firefly luciferase linked therein. The term "biotinated peptide" means a peptide which can be bound to biotin by the action of biotin holoenzyme synthetase.

The present invention further relates to biotinated firefly luciferase having the activity of biotinated firefly luciferase, which comprises an animo acid sequence set forth in Sequence No. 6 or 9 in which one or more amino acids may be added, deleted or replaced.

The present invention further relates to a gene for biotinated firefly luciferase, which comprises a gene coding for a biotinated peptide and a gene for firefly luciferase linked therein.

The present invention further relates to a biotinated firefly luciferase gene, which comprises a firefly luciferase gene and a biotinated peptide gene coding for an amino acid sequence bringing about the activity of a biotinated peptide set forth in Sequence No. 1 or 7 in which one or more amino acids may be added, deleted or replaced.

The present invention further relates to a recombinant DNA, which comprises said biotinated firefly luciferase gene inserted into a vector DNA.

The present invention further relates to a process for producing biotinated firefly luciferase, which comprises culturing a microorganism belonging to the genus Escherichia carrying said recombinant DNA, and then recovering the biotinated firefly luciferase from the culture.

The present invention further relates to a bioluminescent analysis method which comprises using said biotinated firefly luciferase.

The present invention further relates to a bioluminescent analysis method which comprises quantifying a ligand by measuring a biotinated receptor with said biotinated firefly luciferase.

DETAILED DESCRIPTION OF THE INVENTION

Figure 1:
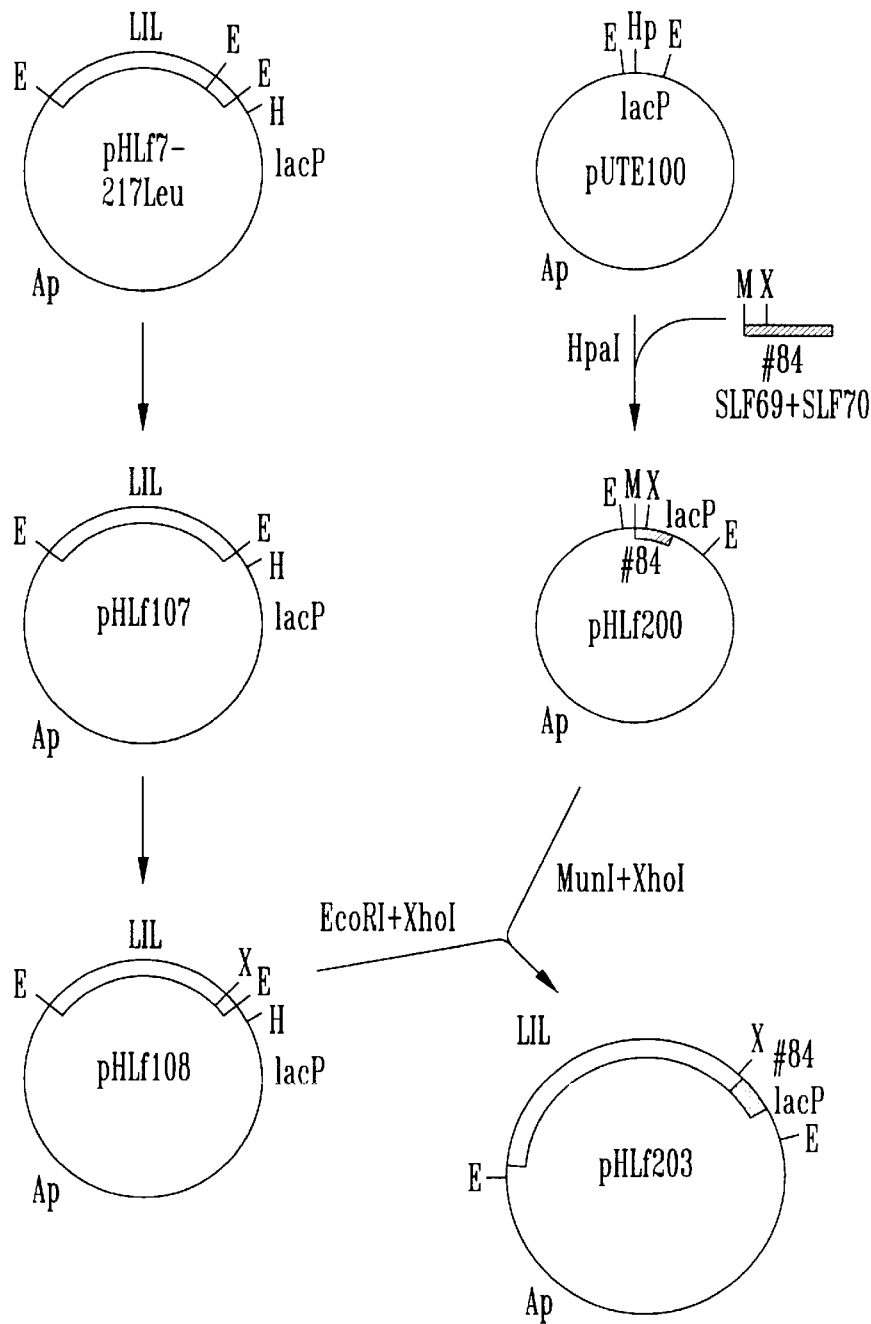
FIG. 1 shows the construction of recombinant plasmid pHLf203 DNA.

As a result of their eager research, the inventors have found that soluble and active biotinated firefly luciferase could be efficiently obtained from the culture of a microorganism belonging to the genus Escherichia carrying a recombinant DNA prepared by inserting into a vector DNA a gene for biotinated firefly luciferase having a biotinated peptide gene coding for an amino acid sequence set forth in Sequence No. 1 or 7 and a firefly luciferase gene linked therein, and also that the biotinated firefly luciferase thus obtained provides a highly sensitive bioluminescent analysis method as compared with chemically modified biotinated firefly luciferase.

Essentially, the present invention involves linking a gene coding for a peptide (biotinated peptide) of from about 10 to about 120 residues to which biotin is bound in cells by the action of biotin holoenzyme synthetase; transforming the resulting gene into a microorganism; and producing a fusion protein in which the biotinated peptide has been biotinated by the action of the biotin holoenzyme synthetase possessed by said microorganism.

In the present invention, the peptide to which biotin is bound in cells by the action of biotin holoenzyme synthetase, i.e. the biotinated peptide, includes e.g. a biotinated lysin residue-containing peptide of 10 to 120 residues from naturally occurring biotin enzyme [e.g. the biotin enzyme described in the Journal of Biological Chemistry, 263, 6461 (1988)] or a biotinated peptide which was artificially created based on such a sequence [e.g. the peptide described in BIO/TECHNOLOGY, 11, 1138 (1993)].

Examples of such biotinated peptides are those of the amino acid sequences of Sequences No. 1 and 7. These peptides can be expected to be subjected without losing their activity to minor modifications of their amino acid sequences. Such modifications of amino acid sequence include the addition, deletion or replacement of one or more amino acids, and those modified peptides which still keep the biotination activity are included in the scope of the biotinated peptides of the invention. Those peptides in which amino acids are added, deleted or replaced can be suitably prepared in a peptide synthetic process known in the art.

As firefly luciferase, mention may be made of luciferase derived from fireflies such as *Luciola cruciata, Luciola lateralis* (both described by N. Kajiyama et al., Biochim. Biophys. Acta, 1120, 228 (1992)], *Luciola mingrelica* [N. Yu. Philippova and N. N. Ugarova, Biokhimiya, 44, 1508 (1979)] and *Photinus pyralis* [M. DeLuca and W. D. McElroy, Meth. Enzymol., 72, 3 (1978)]. Among them, the amino acid sequence of thermostable mutant luciferase derived from HEIKE firefly (*Luciola lateralis*) in which Ala at the 217-position has been replaced by Leu is as shown in Sequence No. 2.

A gene for a biotinated peptide can be synthesized in a DNA synthesizer or can be cloned by the PCR techniques. A gene for firefly luciferase can be cloned by a conventional method [J. Sambrook et al., Molecular Cloning A Laboratory Manual (1989) Cold Spring Harbor Laboratory Press] or by the PCR techniques if the target sequence is known.

The primary sequence of a fusion protein (biotinated firefly luciferase) between a biotinated peptide and firefly luciferase is not limited insofar as the functions of the two peptides are not impaired. That is, either of them may be located at the N-terminal side or one of them may be located within the molecule of the other. A linker sequence such as $(Gly_4Ser)_3$ [J. S. Huston et al., Proc. Natl. Acad. Sci. USA (1988)] or Ser Ser Ala (Asp Asp Ala Lys Lys)$_4$ Asp Gly [M. W. Pantoliano et al., Biochemistry, 30, 10117 (1991)] may also be located between them.

A recombinant can be obtained by linking the gene for biotinated peptide to the gene for firefly luciferase in a conventional method [J. Sambrook et al., Molecular Cloning A Laboratory Manual (1989) Cold Spring Harbor Laboratory Press], ligating the resulting gene for biotinated firefly luciferase in a usual manner to a vector DNA containing a promoter sequence, a marker gene and an origin of replication, and transforming the resulting recombinant DNA into *Escherichia coli,* yeast (*Saccharomyces cerevisiae*), etc.

The vector DNA used includes pUC119 (produced by Takara Shuzo Co., Ltd.), pMA56 [G. Ammerer, Meth. Enzymol, 101, 192 (1983)], or the like.

To produce the biotinated firefly luciferase, microorganisms carrying the above recombinant DNA are cultured in a medium to yield a fusion protein in which the conserved Lys residue in the biotinated peptide has been biotinated by the action of biotin holoenzyme synthetase possessed by the microorganisms. The microorganisms may be cultured in either solid or liquid medium, preferably liquid medium.

As the medium, there is employed the one containing at least one inorganic salt such as sodium chloride, potassium dihydrogen phosphate, dipotassium hydrogen phosphate, magnesium sulfate, magnesium chloride, ferric chloride, ferric sulfate, manganese sulfate, etc. and at least one nitrogen source such as yeast extract, trypton, peptone, meat extract, corn steep liquor, exudate of soybean or wheat bran, etc., if necessary a suitable amount of sugars (or carbohydrates), vitamins, etc.

The initial pH of medium is preferably adjusted within pH 7–9. The microorganisms are cultured at 30° to 42° C., preferably around 37° C., for 3 to 24 hours, preferably 5 to 8 hours, by submerged aeration culture, shake culture, or stationary culture.

For recovery of the biotinated firefly luciferase, the culture supernatant and microorganisms are obtained from the culture after incubation, for example by centrifugation, and the microorganisms are disrupted by ultrasonication or treatment with lytic enzyme. Then, the purification of the biotinated firefly luciferase from the culture supernatant or the disrupted cell solution can be effected by a combination of conventional purification means, such as ammonium sulfate precipitation, gel filtration, ion-exchange chromatography, hydrophobic chromatography, etc. The activity of the biotinated firefly luciferase as fusion protein in the cell supernatant or disrupted cell solution can be determined according to the method described by E. A. Bayer et al. [Anal. Biochem., 154, 367 (1986)] and J. R. De Wet et al. [Meth. Enzymol., 133, 3 (1986)].

The biotinated firefly luciferase thus obtained can be applied to a variety of bioluminescent analysis methods. For example, the biotinated firefly luciferase can be bound through the biotin thereof to avidin or streptavidin to form a luciferase complex, and a luminescent analysis method using such a firefly luciferase complex can be applied to a detection system using biotin-avidin in techniques used frequently at present, such as enzyme immunoassays, DNA probe method, immunostaining, receptor measurement, in situ hybridization, etc. [Enzyme Immunoassay (Protein, Nucleic Acid and Enzyme [Tanpakushitsu Kakusan Koso], Extra No. 31 (1987)) compiled by Tsunehiro Kitagawa and published by Kyoritsu Shuppan; Enzyme Immunoassay (1989) written by P. Tijssen and translated by Eiji Ishikawa and published by Tokyo Kagaku Dojin; DNA Probe (1988) written by Toyozo Takahasi and published by CMC].

EXAMPLE

The present invention is described in more detail with reference to the following example.

1. Construction of a Plasmid for Expression of Biotinated Firefly Luciferase bL203

Two oligonucleotides [SLF69 strand (Sequence No. 3) and complementary SLF70 strand (Sequence No. 4)] coding for biotinated peptide #84 (Met Ala Phe Ser Leu Arg Ser Ile Leu Glu Ala Gln Lys Met Glu Leu Arg Asn Thr Pro Gly Gly Ser) (the Lys residue at the 13-position is assumed to be biotinated by the action of biotin holoenzyme synthetase) [P. J. Shatz, BIO/TECHNOLOGY, 11, 1138 (1993)] and having restriction enzyme XhoI and MunI sites downstream thereof were synthesized in DNA Model 392 synthesizer (manufactured by Applied Biosystems).

1 pmol of each of oligonucleotides SLF69 and SLF70 was phosphorylated with T4 polynucleotide kinase (produced by Takara Shuzo Co., Ltd.) and the two oligonucleotides were annealed at 90° C. for 10 min. and then at 37° C. for 10 min. Separately, plasmid pUTE100 DNA (described in Japanese Patent Application Laid-Open Publication No. 317055/1993) was cleaved with restriction enzyme HpaI and dephosphorylated with alkaline phosphatase (produced Takara Shuzo Co., Ltd.). The cleaved plasmid was ligated to the above annealed oligonucleotide with T4 DNA ligase (produced by Takara Shuzo Co., Ltd.) to give recombinant plasmid pHLf200 DNA having the oligonucleotide coding for biotinated peptide #84 inserted into the HpaI site located downstream from the β-galactosidase promoter in plasmid pUTE100 DNA (see FIG. 1).

Separately, a single-stranded DNA of recombinant plasmid pHLf7-217 Leu [a plasmid prepared by inserting into plasmid pUC119 a gene for thermostable mutant HEIKE firefly luciferase in which Ala at 217-position was replaced by Leu (described in Japanese Patent Application Laid-Open Publication No. 244942/1993), and the amino acid sequence of the thermostable mutant HEIKE firefly luciferase is shown in Sequence No. 2] was prepared using helper phage M13 K07 (produced by Takara Shuzo Co., Ltd.). The EcoRI site in the luciferase gene was removed using oligonucleotide SLF15 (AGGAATAAAGAACTCTTCACAGTT) (SEQ ID NO:10) and Oligonucleotide-Directed In Vitro Mutagenesis System Version 2 (produced by Amersham) without changing the amino acid sequence of the luciferase gene, whereby plasmid pHLf107 DNA was obtained (see FIG. 1). Using oligonucleotide SLF43 (TTCATCGTTCTCGAGGTTTTCCATAGA) (SEQ ID NO:10) (restriction enzyme XhoI site is underlined), a XhoI site was introduced in an analogous manner in the neighborhood of the 5'-terminal of the luciferase gene in recombinant pHLf107 DNA, whereby plasmid pHLf108 was obtained (see FIG. 1).

After pHLf108 was cleaved with restriction enzymes XhoI and EcoRI (both produced by Takara Shuzo Co., Ltd.), a luciferase gene fragment was obtained in agarose gel electrophoresis using a gene clean II kit (produced by BIO101). This fragment was ligated to pHLf200 previously cleaved with XhoI and MunI (both produced by Takara Shuzo Co., Ltd.), to give recombinant plasmid pHLf203 DNA which can initiate the expression of biotinated firefly luciferase bL203 by the β-galactosidase promoter (see FIG. 1). The nucleotide sequence of the biotinated firefly luciferase bL203 gene contained in recombinant plasmid pHLf203 DNA is shown in Sequence No. 5 and the amino acid sequence encoded by said gene is shown in Sequence No. 6.

2. Confirmation of the Production of Biotinated Firefly Luciferase bL203 in *E. coli*

Recombinant plasmid pHLf203 DNA-containing *E. coli* JM101 [pHLf203] [using *E. coli* JM101 (ATCC33876) as host] (*E. coli* JM101 [pHLf203] has been deposited as FERM BP-5052 with the National Institute of Bioscience and Human-Technology, Agency of Industrial Science and Technology, Japan) was cultured at 30° C. for 5 hours with stirring at 120 r.p.m. in 2 ml of LB medium (1% Bactotrypton, 0.5% yeast extract, 0.5% sodium chloride) containing 0.2 mM isopropyl-β-thiogalactoside (IPTG) and 50 μg/ml ampicillin. The bacteria were recovered by centrifugation at 5,000 r.p.m. for 5 min., disrupted by ultrasonication and centrifuged at 12,000 r.p.m. for 5 min., to give a supernatant of the disrupted bacteria.

The supernatant of the disrupted bacteria was determined for the activity of biotinated firefly luciferase bL203 in the following manner. Each well in microtiter immunoassay plate FluoroNunc Plate C96 White Maxisorp (manufactured by Nunc), was charged with 100 μl biotinated bovine serum albumin (BSA) solution [10 μg/ml ALBUMIN BOVINE-BIOTIN Labeled (SIGMA), 15 mM sodium carbonate (pH 9.6)], and the plate was allowed to stand at 4° C. for 16 hours to immobilize the biotinated BSA. The biotinated BSA solution was discharged from the well and each well was washed with 300 μl of TPBS [0.05% Tween 20, 65 mM sodium chloride, 10 mM sodium phosphate (pH 7.2)], and then 300 μl blocking solution [1% BSA, 65 mM sodium chloride, 10 mM sodium phosphate (pH 7.2)] was added thereto and allowed to stand at 37° C. for 2 hours to block the well. After the blocking solution was discharged, each well was washed with 300 μl of TPBS, then charged with 100 μl of 10 μg/ml avidin (produced by Wako Junyaku) dissolved in PBS or with an equal volume of PBS as the control, and allowed to stand for 1 hour at room temperature. Each well was washed with TPBS, and 100 μl of a 10-fold dilution in PBS of the above supernatant of the disrupted *E. coli* JM101 [pHLf203] was added thereto and allowed to stand for 1 hour at room temperature. The dilution of the supernatant of the disrupted bacteria was discharged and each well was washed 4 times with 300 μl of TPBS.

The luciferase activity of each well was determined in the following manner. The microtiter immunoassay plate was attached to Microplate Luminometer ML3000 (manufactured by DYNATECH), and 100 μl substrate solution [0.069 mM luciferin (produced by SIGMA), 4 mM ATP, 4.3 mM magnesium chloride, 25 mM glycylglycine (pH 7.8)] was added thereto and the number of photons generated during 20 seconds was determined. The result showed that while the emission in the well to which avidin had not been added was 96 counts, the emission in the well to which avidin had been added was 27,000 counts, indicating the significant increase of the activity of luciferase. Hence, the production of firefly luciferase having the ability to bind to avidin, i.e. active biotinated firefly luciferase bL203 in the supernatant of the disrupted bacteria *E. coli* JM101 [pHLf203] was confirmed.

3. Purification of Biotinated Firefly Luciferase bL203

*E. coli* JM101 [pHLF203] was cultured at 30° C. with stirring at 120 r.p.m. for 5 hours in 1 liter of LB medium (1% Bacto-trypton, 0.5% yeast extract, 0.5% sodium chloride) containing 0.2 mM isopropyl-β-thiogalactoside (IPTG), 50 μg/ml ampicillin and 10 μg/ml D-biotin. The bacteria were recovered by centrifugation at 5,000 r.p.m. for 5 min. and suspended in 100 ml buffer [25 mM tris(hydroxymethyl) aminomethane (Tris), 1 mM ethylenediaminetetraacetic acid (EDTA), 10% saturated ammonium sulfate, 1 mg/ml lysozyme, pH 7.8]. The bacteria were lysed by being frozen and melted 3 times and centrifuged at 12,000 r.p.m. for 5 min. to give a supernatant of the disrupted bacteria solution. The purification of bL203 from the supernatant of the disrupted bacteria solution was conducted according to the method described by Kajiyama et al. [N. Kajiyama et al., Biochim. Biophys. Acta, 1120, 228 (1992)]. The concentration of the purified bL203 was determined by measuring ultraviolet absorption. The specific activity of the purified bL203 was 98% relative to that of the purified thermostable HEIKE firefly luciferase in which Ala at the 217-position was replaced by Leu. The activity of the purified bL203 was not lost even after more than 60-days storage at 4° C.

4. Preparation of Chemically Modified Biotinated Firefly Luciferase

In order to compare with biotinated firefly luciferase bL203 of the present invention, chemically modified biotinated firefly luciferase was prepared according to the method of Japanese Patent Laid-Open Publication No. 138463/1985. According to the publication, the firefly luciferase used was the firefly luciferase derived from *Photinus pyralis* obtained from Sigma Chemical. To 400 μl of 2.6 mg/ml firefly luciferase in a reaction buffer [0.1M sodium chloride, 0.1M potassium phosphate (pH 7.6)] were added 592 μl of 5.5 μM ATP solution in the same buffer and 60 nmol N-hydroxysuccinimide biotin (produced by Pierce) in 8 μl dimethylsulfoxide. After overnight incubation at 4° C., the sample was dialyzed against a buffer [10% glycerol, 1 mM EDTA, 2 mM β-mercaptoethanol, 0.1M potassium phosphate (pH 7.5)]. The activity of this labeled firefly luciferase was 62% relative to the unmodified firefly luciferase, and the chemically modified firefly luciferase with at least 50% activity was obtained as described in the above publication, but this activity was far from 98% attained by the biotinated firefly luciferase obtained in the method of the present invention.

5. Change in the Activity by Binding to Streptavidin

The change in the activity upon binding to streptavidin was compared between biotinated firefly luciferase bL203 and the chemically modified biotinated firefly luciferase. 0.1 ng/ml of each biotinated firefly luciferase in a luciferase diluent [1% BSA, 1 mM EDTA, 1 mM β-mercaptoethanol, 50 mM HEPES (pH 7.5)] was mixed with an equal volume of 1 μg/ml streptavidin (Boehringer Mannheim GmbH) in the luciferase diluent or with the luciferase diluent as the control and allowed to stand for 30 min. at room temperature. 50 μl of each sample solution was put to a well on Microtiter Plate Microlite 2 (produced by Dynatech Laboratories) which was then attached to a microplate reader LUMINOUS CT-9000D (DIA IATRON) for bioluminescent and chemiluminescent measurements, and 50 μl substrate solution [40 mM ATP, 1.4 mM luciferin, 300 mM magnesium sulfate, 50 mM HEPES (pH 7.5)] was put to each well and the number of photons generated for 10 seconds was determined. The result showed that after mixed with streptavidin, the remaining activities of biotinated firefly luciferase bL203 and the chemically modified biotinated firefly luciferase were 93% and 62%, respectively, indicating that the change of the activity was small in the case of the biotinated firefly luciferase bL203 of the present invention, while nearly 40% of the activity was lost in the case of the chemically modified biotinated firefly luciferase.

6. Sandwich ELISA using Biotinated Firefly Luciferase bL203

100 μl of 5 μg/ml goat anti-mouse IgG Fc fragment-specific polyclonal antibody (produced by Jackson Immuno Research) in 50 mM sodium carbonate buffer (pH 9.6) was put to each well in microtiter plate Microlite 2 and immobilized at 4° C. overnight. Each well was washed 4 times with 300 μl of T-TBS [0.05% Tween 20, 0.15M NaCl, 50 mM Tris (pH 7.6)], then charged with 200 μl of a 4-fold dilution of Blockace (produced by Dainippon Seiyaku) and blocked at 4° C. overnight. The well was washed in the same manner, then charged with 100 μl of 1 pg/ml to 1000 pg/ml mouse $IgG_1$ (produced by Chemicon) in a 4-fold dilution of Blockace or with 100 μl of a 4-fold dilution of Blockace as the negative control and allowed to stand at 37° C. for 2 hours. After washing, 100 μl of 0.1 μg/ml biotinated goat anti-mouse IgG F(ab')$_2$ fragment-specific polyclonal antibody F(ab')$_2$ fragment (produced by Jackson Immuno Research) in a 4-fold dilution of Blockace was added thereto and allowed to stand at 37° C. for 1 hour. After washing, 100 μl of 2 μg/ml streptavidin (Boehringer Mannheim GmbH) in a 4-fold dilution of Blockace was added thereto and allowed to stand at room temperature for 30 min. After washing, 100 μl of 5×10$^{-13}$ mol/ml biotinated firefly luciferase bL203 or the chemically modified biotinated firefly luciferase in the luciferase diluent was added thereto and allowed to stand at room temperature for 30 min. After washing, 50 μl luciferase diluent [1% BSA, 1 mM EDTA, 1 mM β-mercaptoethanol, 50 mM HEPES (pH 7.5)] was put to each well and then the plate was attached to a microplate reader LUMINOUS CT-9000D (DIA IATRON) for bioluminescent and chemiluminescent measurements. 50 μl substrate solution [40 mM ATP, 1.4 mM luciferin, 300 mM magnesium sulfate, 50 mM HEPES (pH 7.5)] was added to each well and the number of photons generated for 10 seconds were determined as shown in Table 1.

TABLE 1

| mouse $IgG_1$ concentration (pg/ml) | emission with biotinated firefly luciferase bL203 (counts) Note[1] | emission with chemically modified biotinated firefly luciferase (counts) Note[1] |
| --- | --- | --- |
| 0 | 5633 | 131 |
| 1 | 5773 | 156 |
| 5 | 6906 | 151 |
| 10 | 7781 | 158 |
| 50 | 16319 | 196 |
| 100 | 24950 | 241 |
| 1000 | 162429 | 1117 |

Note[1]: mean value of 4 wells measurements

As is evident from Table 1, biotinated firefly luciferase bL203 could be used for measurements from 5 pg/ml (P<0.05) according to the Student's t test [R. C. Canbel: Introduction to Statistics for Biologists (2nd edition) (1976), translated into Japanese by Susumu Ishii and published by Baifukan], while the chemically modified biotinated firefly luciferase could be used for measurements from 50 pg/ml with a significant difference (P<0.05). From the foregoing, it became evident that the biotinated firefly luciferase of the present invention attains 10 times sensitivity as high as the conventional chemically modified biotinated firefly luciferase.

7. Construction of a Plasmid for Expression of Biotinated Firefly Luciferase bL248

It is known that a biotin carboxyl carrier protein (referred to hereinafter as BCCP) as a subunit of acetyl CoA carboxylase from E. coli is biotinated at the Lys residue at the 122-position by the action of biotin holoenzyme synthetase in E. coli [The Journal of Biological Chemistry, 263, 6461 (1988)]. A gene coding for a biotinated Lys residue-containing polypeptide consisting of 87 residues of the C-terminal side of BCCP (referred to hereinafter as BCCP-87, Sequence No. 7) was cloned in the following manner. According to the method described in Japanese Patent Application Laid-Open Publication No. 292584/1994, genomic DNA was obtained from E. coli 1100 (obtained from Max-Plank-Institute, Heidelberg, Germany) and denatured. On the basis of the nucleotide sequence of the BCCP gene reported by S. Muramatsu et al. [Nucleic Acids Research, 17, 3982 (1989)], oligonucleotide SLF116 (CCGGCGACCGTTGGATCCATGGAAGCG) (SEQ ID NO:12) as the 5'-terminal primer and oligonucleotide SLF117 (TTATCCAGCGGATCCACTAGTTTAC TCGATGACGACCAGCGG) (SEQ ID NO:13) as the 3'-terminal primer were synthesized in DNA model 392 synthesizer (manufactured by Applied Biosystems). For subsequent subcloning, restriction enzyme BamHI recognition site (underlined) was introduced to each primer. 1 pmol of each of primer SLF116 and primer SLF117 and 0.1 μg of the above denatured genomic DNA from E. coli were subjected to PCR amplification using DNA Thermal Cycler (produced by Perkin-Elmer) and a GeneAmp PCR reagent kit containing Ampli Taq DNA polymerase (produced by Takara Shuzo Co., Ltd.) to give 1 μg of a gene fragment coding for BCCP-87 which was then digested with BamHI.

Figure 2:
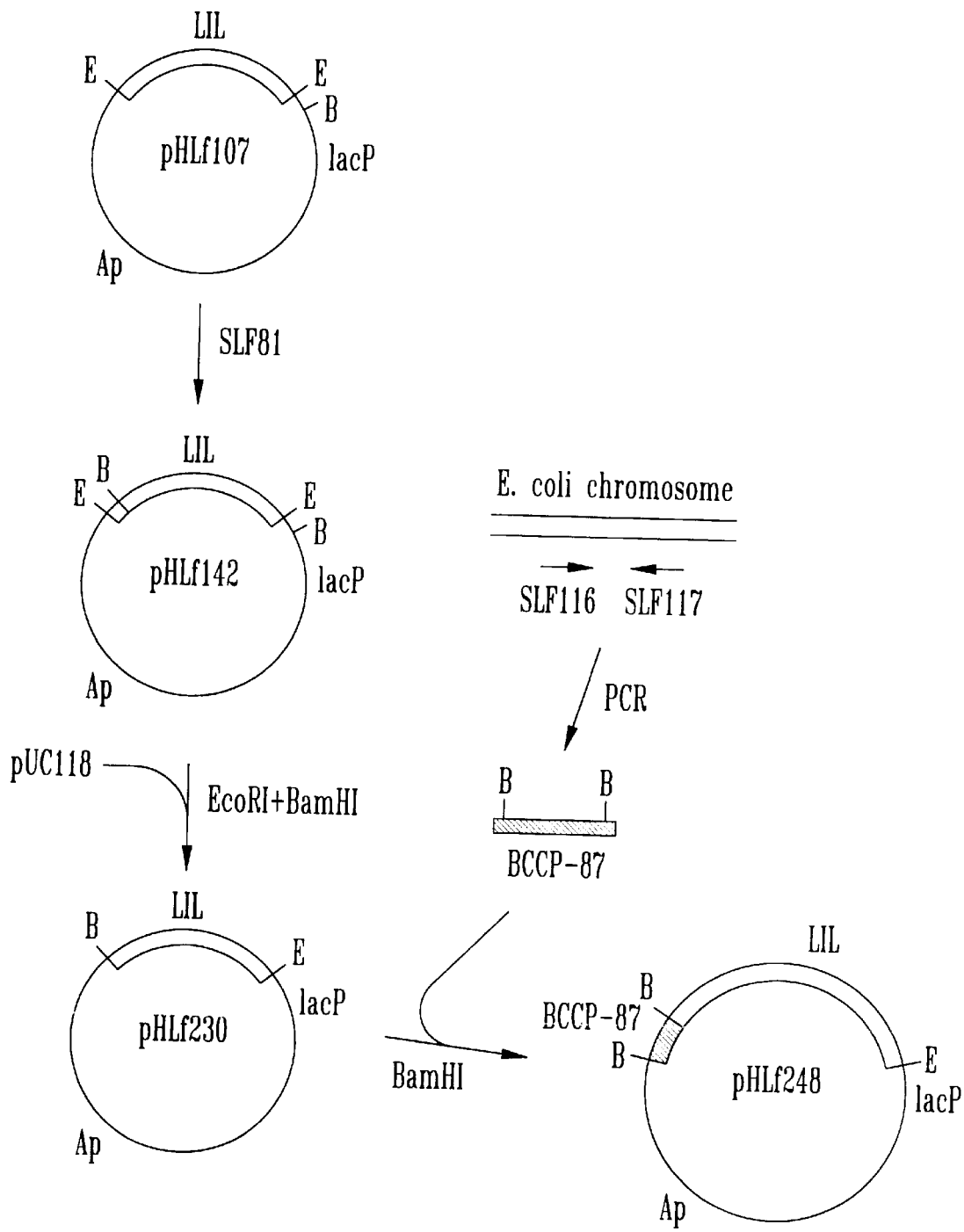
FIG. 2 shows the construction of recombinant plasmid pHLf248 DNA.

Separately, plasmid pHLf142 DNA was obtained in which a BamHI site was introduced in the neighborhood of the 3'-terminal of the luciferase gene in plasmid pHLf107 DNA (see FIG. 1) by site-specific mutation described in item 1 above using oligonucleotide SLF81 (TGATTGACATGGATCCCTTAGCAACT) (SEQ ID NO:14) (restriction enzyme BamHI site is underlined) (see FIG. 2). Then, plasmid pHLf142 DNA was completely digested with restriction enzymes BamHI and EcoRI (both produced by Takara Shuzo Co., Ltd.) and subjected to agarose gel electrophoresis. Then a luciferase gene fragment was prepared using a gene clean II kit (produced by BIO101). This fragment was ligated to plasmid pUC118 DNA (produced by Takara Shuzo Co., Ltd.) previously cleaved with BamHI and EcoRI, whereby plasmid pHLf230 DNA was constructed (see FIG. 2).

Plasmid pHLf230 DNA was cleaved with BamHI and then ligated in a usual manner to the above BamHI-digested BCCP-87 gene fragment, to give recombinant plasmid pHLf248 DNA capable of initiating by the β-galactosidase promoter the expression of biotinated firefly luciferase bL248 having BCCP-87 fused with the C-terminal of thermostable HEIKE firefly luciferase (Sequence No. 2) (see FIG. 2). The nucleotide sequence of the biotinated firefly luciferase bL248 gene contained in recombinant plasmid pHLf248 is shown in Sequence No. 8 and the amino acid sequence encoded by said gene is shown in Sequence No. 9.

8. Confirmation of the Production of Biotinated Firefly Luciferase bL248 in *E. coli*

*E. coli* JM101 [pHLf248] carrying recombinant plasmid pHLf248 DNA [using *E. coli* JM101 (ATCC33876) as host] [*E. coli* JM101 [pHLf248] has been deposited as FERM BP-5081 with the National Institute of Bioscience and Human-Technology, Agency of Industrial Science and Technology, Japan] was cultured and the activity of the biotinated luciferase was determined according to the same manner as in item 2 above. The result indicated that while the emission in the well to which avidin had not been added was 75 counts, the emission in the well to which avidin had been added was 11,000 counts, indicating that *E. coli* JM101 [pHLf248] produced active biotinated firefly luciferase bL248.

9. Partial Purification of Biotinated Firefly Luciferase bL248

According to the method described in item 3, *E. coli* JM101 [pHLf248] was cultured and a supernatant was obtained from the disrupted microorganism. According to the method described by Kajiyama et al. (N. Kajiyama et al., Biochem. Biophys. Acta, 1120, 228 (1992)), a fraction precipitated in the supernatant between 30–60% saturated ammonium sulfate was obtained and suspended in a buffer (25 mM Tris, 1 mM EDTA, 10% saturated ammonium sulfate, pH 7.8) and this solution was served as crude purified preparation. Biotinated firefly luciferase bL248 upon binding to streptavidin maintained 102% activity as determined according to the method described in item 5 above, indicating that the activity was not lost even after binding to streptavidin.

10. Sandwich ELISA using Biotinated Firefly Luciferase bL248

The above crude enzyme solution of biotinated firefly luciferase bL248 was used for quantification of mouse $IgG_1$ by sandwich ELISA according to the method described in item 6 above (Table 2). The amount of biotinated firefly luciferase bL248 was the same in terms of activity as that of biotinated firefly luciferase bL203 used in item 6. As is evident from Table 2, biotinated firefly luciferase bL248 could be used for measurements from 10 pg/ml ($P<0.05$) according to Student's t test and attained 5 times sensitivity as high as the limit of measurement (50 pg/ml) of the conventional chemically modified biotinated firefly luciferase (Table 1).

TABLE 2

| mouse $IgG_1$ concentration (pg/ml) | emission with biotinated firefly luciferase bL248 (counts) Note[1] |
|---|---|
| 0 | 379 |
| 1 | 376 |
| 5 | 394 |
| 10 | 458 |
| 50 | 856 |
| 100 | 1393 |
| 1000 | 11219 |

Note[1]: mean value of 4 wells measurements

---

What is claimed is:

1. A biotinated fusion protein having the amino acid sequence of SEQ ID NO: 6 or 9.

2. The fusion protein of claim 1, which has the amino acid sequence of SEQ ID NO: 6.

3. The fusion protein of claim 2, wherein the Lys residue at position 13 in the amino acid sequence of SEQ ID NO: 6 is biotinated.

4. The fusion protein of claim 1, which has the amino acid sequence of SEQ ID NO: 9.

5. The fusion protein of claim 4, wherein the Lys residue at position 602 in the amino acid sequence of SEQ ID NO: 9 is biotinated.

6. A method for bioluminescent analysis, comprising the steps of:
   (a) contacting the fusion protein of claim 1 with a receptor comprising avidin or streptavidin; and
   (b) detecting the emission from the fusion protein.

7. A method for bioluminescent analysis, comprising the steps of:
   (a) contacting the fusion protein of claim 2 with a receptor comprising avidin or streptavidin; and
   (b) detecting the emission from the fusion protein.

8. A method for bioluminescent analysis, comprising the steps of:
   (a) contacting the fusion protein of claim 3 with a receptor comprising avidin or streptavidin; and
   (b) detecting the emission from said the fusion protein.

9. A method for bioluminescent analysis, comprising the steps of:
   (a) contacting the fusion protein of claim 4 with a receptor comprising avidin or streptavidin; and
   (b) detecting the emission from said the fusion protein.

10. A method for bioluminescent analysis, comprising the steps of:
    (a) contacting the fusion protein of claim 5 with a receptor comprising avidin or streptavidin; and
    (b) detecting the emission from said the fusion protein.

* * * * *